United States Patent [19]
Buckles et al.

[11] 3,993,069
[45] Nov. 23, 1976

[54] LIQUID DELIVERY DEVICE BLADDER

[75] Inventors: Richard G. Buckles, Redwood City; Harold M. Leeper, Mountain View; Su Il Yum, Sunnyvale; Alan S. Michaels, Atherton, all of Calif.

[73] Assignee: Alza Corporation, Palo Alto, Calif.

[22] Filed: Aug. 18, 1975

[21] Appl. No.: 605,690

Related U.S. Application Data

[63] Continuation-in-part of Ser. No. 344,713, March 26, 1973, abandoned.

[52] U.S. Cl. ............. 128/214 F; 128/DIG. 12; 222/386.5; 222/215; 222/107
[51] Int. Cl.² ............. A61M 5/00; B65D 35/18
[58] Field of Search ............. 128/213, 214 F, 216, 128/DIG. 12; 222/386.5, 215, 94, 212, 107, 206, 95; 220/63 R, 85 B; 260/79.5 A, 79.5 B; 46/87

[56] References Cited
UNITED STATES PATENTS

| | | | |
|---|---|---|---|
| 2,378,030 | 6/1945 | Olin | 260/79.5 B |
| 2,816,690 | 12/1957 | Lari | 222/92 |
| 2,876,768 | 3/1959 | Schultz | 128/DIG. 12 |
| 3,200,174 | 8/1965 | Adamek et al. | 260/79.5 A |
| 3,412,906 | 11/1968 | Dinger | 128/214 F |
| 3,469,578 | 9/1969 | Bierman | 128/216 |
| 3,486,539 | 12/1969 | Jacuzzi | 128/DIG. 12 |
| 3,506,005 | 4/1970 | Gilio et al. | 128/214 F |
| 3,642,727 | 2/1972 | Ashworth | 260/79.5 A |
| 3,677,444 | 8/1972 | Merrill | 222/215 |
| 3,791,557 | 2/1974 | Venus, Jr. | 222/386.5 |

FOREIGN PATENTS OR APPLICATIONS 650,165  10/1962  Canada ............. 220/85 B

*Primary Examiner*—Stephen C. Pellegrino
*Attorney, Agent, or Firm*—Thomas E. Ciotti; Paul L. Sabatine; Edward L. Mandell

[57] ABSTRACT

An improvement in liquid dispensers, especially those used to infuse liquid drugs into patients from an expansible elastomeric bladder of specific geometry and elastomeric properties, is disclosed. The improvement is in making the bladder from an elastomeric composition whose stress relaxation does not exceed 10%, and whose low frequency hysteresis does not exceed 10%.

6 Claims, 9 Drawing Figures

LIQUID DELIVERY DEVICE BLADDER

CROSS-REFERENCE TO RELATED APPLICATION

This application is a continuation-in-part of application Ser. No. 344,713, filed Mar. 26, 1973, now abandoned.

BACKGROUND OF THE INVENTION

1. Field of the Invention

This invention relates to an improvement in an apparatus for delivering liquids under pressure generated by an elastomeric bladder. More particularly, it relates to an improvement in the elastomeric bladder of such an apparatus.

2. Description of the Prior Art

It is well known that when a liquid is pressured into an elastic container so as to distend the container walls, these elastic walls apply pressure to the liquid. This pressure may be used to propel the liquid out of the container. This relationship finds embodiment in such diverse items as water balloons, pressure accumulators (see U.S. Pat. No. 2,480,558, issued Aug. 30, 1949 to DeKiss), sprayers (see U.S. Pat. No. 3,083,871, issued Apr. 2, 1963 to Jepson), pressure pack barrels (see U.S. Pat. No. 2,816,590, issued Dec. 17, 1957 to Lari), intravenous infusion devices (see U.S. Pat. No. 3,486,539, issued Dec. 30, 1969 to Jacuzzi, and U.S. Pat. No. 3,469,578, issued Sept. 30, 1967 to Bierman), and non-aerosol dispensers (see U.S. Pat. No. 3,791,557, issued Feb. 12, 1974 to Venus, Jr.). All of these fluid delivery devices share the same basic structure. Each has a distensible elastic bag or bladder which applies pressure to an enclosed liquid and forces this liquid through a valve which modulates the rate of flow of liquid from the bladder.

Many of these devices function suitably in very crude forms. In other cases it is necessary that the devices be refined to provide an accurately controlled flow of liquid. The present invention relates to an improved elastic bladder for use in fluid delivery devices of the type described hereinabove. The bladder of this invention gives better liquid discharge characteristics than bladders employed heretofore and would find primary application in those devices where precise control of fluid flow is an object.

SUMMARY OF THE INVENTION

The invention is an improvement in a liquid dispensing apparatus that dispenses fluid from an expansible, elastomeric bladder. The appratus to which the improvement relates comprises in combination: a housing; an expansible elastomeric bladder contained within the housing for holding the liquid under pressure, the elastic force in the bladder walls providing the force by which liquid is dispensed from the apparatus; a liquid flow passageway extending from the bladder to a dispensing site; and valve means within said passageway for regulating the flow of liquid through said passageway. The bladder of the apparatus is cylindrical, has a deflated length that is not less than 5 times its deflated inside diameter, walls whose thickness is from 0.01 to 1 times the deflated inside diameter of the bladder, and an axial stress at 300% elongation that is not more than 1.5 times the radial stress at 300% elongation, and is formed of an elastomeric composition that has a permanent set of less than about 3% and that has a uniaxial stress/strain curve that has an ultimate strain exceeding 400%, and a point in the range of 300% and 1000% elongation at which the slope increases significantly.

The improvement in the above apparatus is in making the bladder from an elastomeric composition whose stress relaxation does not exceed about 10% and whose low frequency hysteresis does not exceed about 10%. A further improvement is in housing the bladder within the housing in a manner in which it is substantially unrestricted in its deflated and inflated states.

The above described improvements provide an apparatus that has unexpectedly superior performance as regards constancy of pressure and the percentage of liquid volume that is dispensed. Specifically, its performance is distinguished by the following characteristics:

1. The pressure on the liquid remains constant (within $\pm$ 10% of the mean pressure) during the discharge of up to about 90% of the bladder contents, even when the discharge is at a very slow rate, say 0.1–1.0 ml/hr, 2. The discharge includes at least 95% of the initial contents, and 3. The discharge retains these desirable characteristics (1 and 2 above) even when the discharge is prolonged or delayed over substantial periods of time such as up to 30 hours.

DETAILED DESCRIPTION OF THE INVENTION

Figure 1:
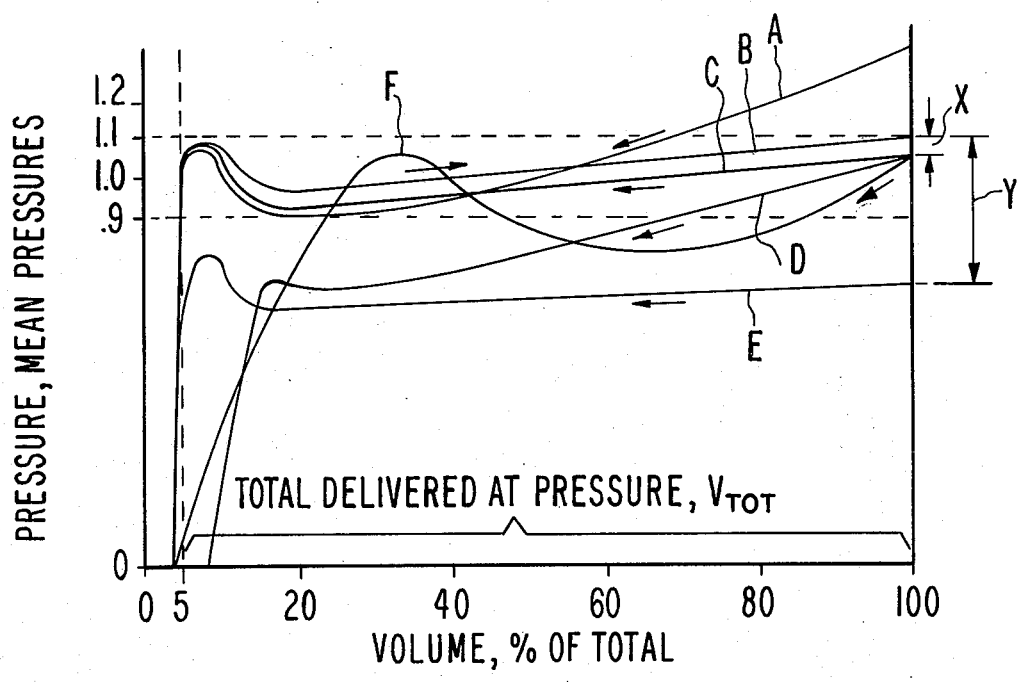
FIG. 1 is a graph illustrating a series of pressure/volume curves of bladders in accord and not in accord with the present invention.

Bladders in accord with this invention have deflation pressure/volume curves in accord with Curve C of FIG. 1. As liquid is pumped into the bladder in an amount measured in per cent of total volume to be introduced, the bladder walls impart a pressure on the enclosed liquid following Curve B, As the bladder remains in an inflated condition, there occurs a loss in pressure as shown by X or Y in FIG. 1. This pressure loss is attributable to the loss of elastic energy (stress) that occurs in the elastomer that forms the bladder while the elastomer is in a stretched state. As the bladder of this invention deflates or pumps out liquid, it follows Curve C. The mean pressure on the liquid as the bladder deflates is defined as $$P_{(m)} = \frac{1}{V_{TOT}} \int_0^{V_{TOT}} P dV$$

wherein $P_{(m)}$ = mean pressure, $P$ = pressure, $V$ = volume, and $V_{TOT}$ = the total volume delivered.

$P_{(m)}$ has a value defined as 1.0 mean pressures. In accord with this invention, the deflation curve must be such that the pressure, during the delivery of up to about 90% of $V_{TOT}$, does not vary by more than ± 0.1 $P_{(m)}$. Curve C meets this criterion. Curves A, D and F are examples of curves which do not fit this criterion. If the pressure variation from $P_{(m)}$ is more than 10%, it is not possible to obtain the constant rates of delivery of liquid from the devices which are required by the present invention.

In the present case, $V_{TOT}$ must equal at least 0.95 (95%) times the total volume of liquid in the inflated bladder. In other words, the residual volume of liquid left in the bladder after the bladder has deflated must be less than 5% of the volume of liquid charged to the bladder. This limit is critical as it relates to the amount of drug left behind when the bladder has pumped out its contents and is consistent with current industrial standards. Curve D illustrates a deflation pattern wherein this critical limit is exceeded. This residual volume is equal to the sum of the dead volume of the deflated bladder initially plus the increase in dead volume which results from the bladder not returning to its initial uninflated dimensions due to permanent set of the elastomer. A bladder which exceeds this limitation is unacceptable as it requires the discarding of a significant portion of the bladder contents, which in the case of drugs, agents and the like can be most costly.

The manner in which the bladder of this invention inflates is important to realizing the above performance criteria. FIGS. 2, 4, 5, 6 and curve B of FIG. 1 illustrate this manner of inflation. FIGS. 2, 4, 5, and 6 depict a liquid dispensing device 10 having an expandable elastomeric bladder 11 of approximate length L. Bladder 11 is mounted to frame 12 by being affixed to tubing connector 14 with clamp 15. The connector 14 is hollow and communicates between bladder 11 and adjustable valve 16 which in turn connects to tube 17. Fluid may be pressured through tube 17 and valve 16 to charge bladder 11 or may be discharged from bladder 11 through valve 16. The first fluid added to bladder 11 merely fills the void volume, the pressure remaining zero and the shape of bladder 11 undergoing no marked change. Next, a small degree of general inflation of bladder 11 occurs both in the axial and radial directions (but predominantly in the radial direction). The volume does not change appreciably, but the pressure rises markedly, as shown in the left hand portion of Curve B in FIG. 1.

Figure 4:
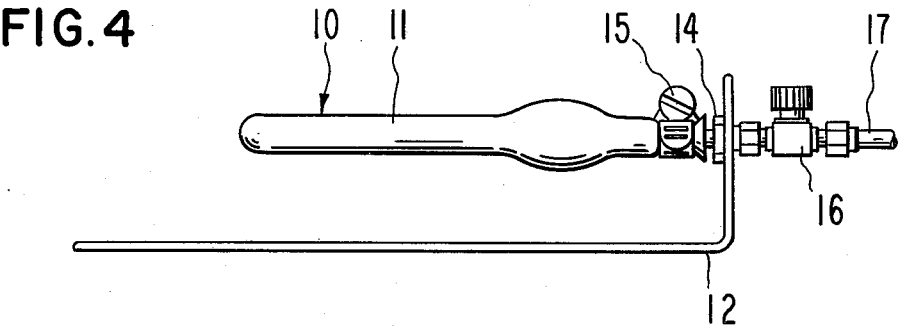
FIGS. 4 and 5 are elevational views of the bladder depicted in FIG. 3, partially inflated.
Figure 5:
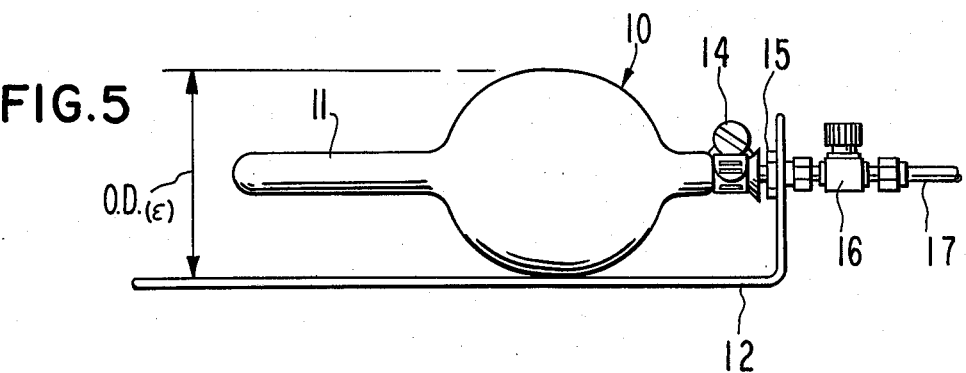
Figure 6:
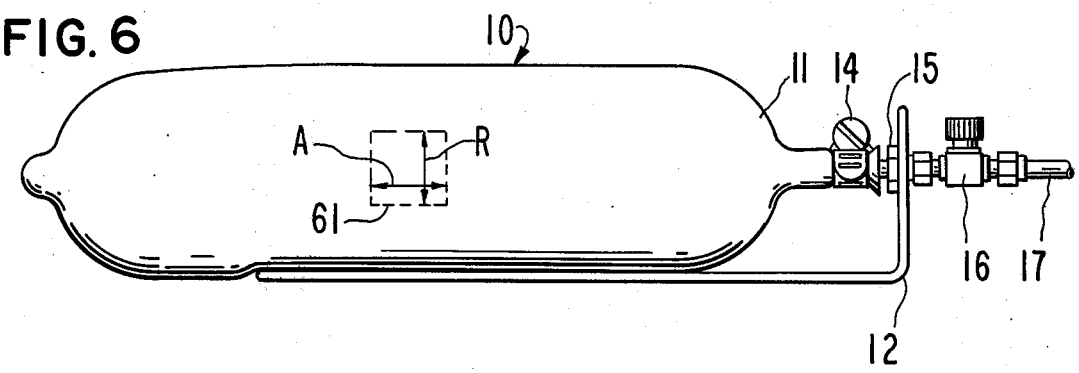
FIG. 6 is an elevational view of the bladder depicted in FIG. 2, inflated.

Next, as more fluid is added, the bladder begins a localized enlargement of a substantially elliptical axial cross section as shown in FIG. 4. The pressure peaks and begins to drop as shown in FIG. 1, Curve B. The bladder is locally changing from its initial substantially thick-walled configuration to a configuration having a wall thickness of substantially less than its I.D. The bladder continues to expand locally, as shown in FIG. 5, until the local expansion reaches an essentially spherical shape. The diameter of this sphere in FIG. 5 will be a set, reproducible value limited by the radial expansion characteristics of the bladder, which are dependent on the elastomer employed, wall thickness and initial bladder diameter. When this sphere has been formed, the pressure in FIG. 1 has dipped to the bottom of the valley of Curve B. As more liquid is added, the sphere begins to expand substantially exclusively in the axial direction, as shown in FIGS. 5 and 6, taking on an oval axial cross section. The pressure is substantially constant, as shown in the middle portion of Curve B of FIG. 1. Near full inflation there is a general tendency for the pressure to rise. The bladder is not inflated past that point.

The geometry of the bladder and certain properties of the elastomer from which the bladder is made are critical to having the bladder inflate in the above described manner and to achieving the above bladder performance criteria. In this regard, the prior art generally failed to recognize any quantitative correlation between bladder performance and bladder geometry/elastomer properties. By happenstance prior art bladders, such as the bladder of the Jacuzzi patent mentioned above, had geometries that fell within the geometrical requirements of the bladders of this invention and were made from elastomers that met some, but not all, of the physical property requirements of the elastomers from which the bladders of this invention are made.

Figure 2:
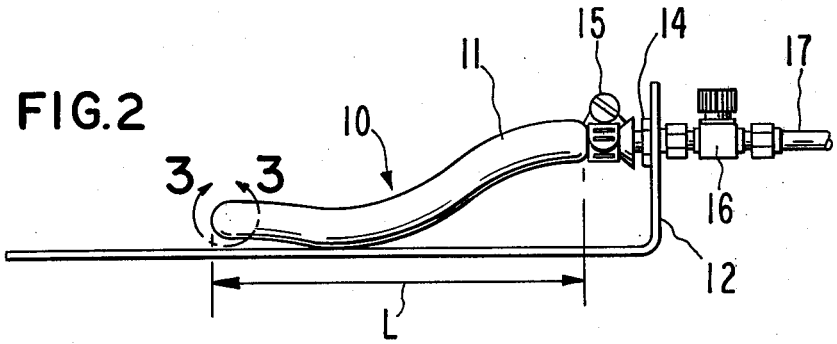
FIG. 2 is an elevational view of a most basic embodiment of the bladder of this invention in deflated form.
Figure 3:
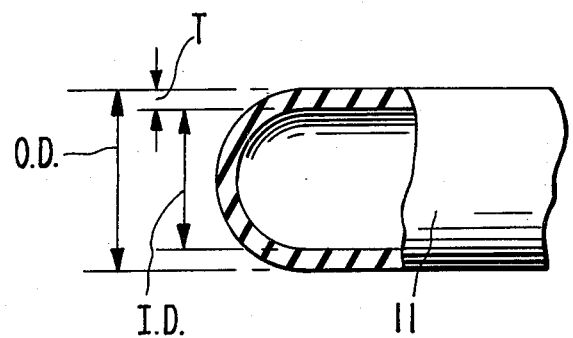
FIG. 3 is an enlarged cut-away view of a portion of the bladder shown in FIG. 2.

A bladder of this invention must have certain geometrical relationships; namely, it is generally cylindrical in its deflated state, its deflated length must be 5 or more times its deflated inside diameter, and the thickness of its walls must be from 0.01 to 1 times, preferably 0.1 to 0.5 times, its deflated inside diameter. The cylindrical shape and the length/inside diameter relationship are important to achieving constancy of deflation pressure. The wall thickness/inside diameter relationship is important to achieving deflation pressures of practical magnitude. This geometry is illustrated in FIGS. 2 and 3. FIG. 3, an enlarged cut-away from bladder 11 at A, sets forth the O.D., I.D., and thickness of the walls (T). The I.D., taken to scale, is not larger than 1/5 L (from FIG. 2) and T is approximately 0.16 times the I.D. (from FIG. 3).

A curve of the shape of Curve F of FIG. 1 results when the bladder is of the wrong geometry. As will be appreciated, Curve F depicts a non-constant pressure during discharge. A curve of the nature of Curve F results when the deflated length of the cylindrical bladder is less than 5 times the deflated inside diameter.

Another criterion of the elastomeric bladders of the present invention concerns the relationship between their axial and radial uniaxial stress/strain curves. A sample of elastomer, such as sample 61, taken from device 10 of FIG. 6, must have a uniaxial stress at 300% strain (i.e., along the A direction of sample 61) which is not more than 1.5 times the radial stress at 300% strain (i.e., along the R direction). If this criterion is not met, the bladder will tend to inflate excessively in the radial direction relative to the axial direction. This may affect constancy of deflation pressure adversely.

The elastomers from which the bladders of this invention are made must have a permanent set at break of less than about 3%. This criterion is important to achieving at least 95% discharge of the liquid charged to the bladder. Permanent set at break is determined by ASTM D412-68. Permanent set at break is the extension remaining after a specimen has been stretched to rupture and the resulting pieces allowed to retract for 10 minutes, expressed as a percentage of original length.

Figure 7:
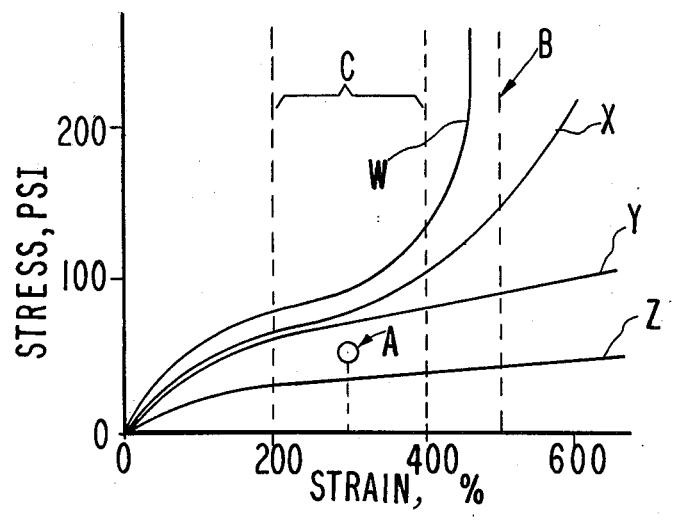
FIG. 7 is a graph illustrating the uniaxial stress/strain curve required for elastomers employed in the bladders of this invention.

Also the uniaxial stress/strain curve of the elastomer must have an ultimate strain (or elongation) of greater than 400%. Turning to FIG. 7, that means that the curve must, like Curve X, pass through line B and not tail upward as does Curve W. Additionally, there must be a point in the curve between 300% and 1000% elongation at which the slope of the curve increases significantly. In most instances this point will be manifested by the beginning point of a substantial discontinuity in the plot of the second derivative of the curve. The ultimate strain and point of increasing slope requirements are related. They indicate that the material has an appropriate balance of "ideal elastomer" properties and self-reinforcement properties. An "ideal elastomer" does not have an inflection point and follows a curve shaped essentially like Curve Y. An elastomer having substantial self-reinforcement properties will follow a curve like Curve W. Only when the two properties are balanced does the stress/strain curve follow Curve X. If these criteria are not met, the resulting bladders will be susceptible to failures. More importantly, they will lack an adequate reserve within the reinforcement zone. This will mean that inflation will not propagate as is desired in an axial direction, as shown in FIGS. 5 and 6, because there will not be sufficient reinforcement to counter radial elongation. Also, it is preferred that the elastomer have a uniaxial stress at 300% elongation that is greater than 50 psi. That is, referring to FIG. 7, the stress/strain curve passes above point A and not below it as does Curve Z. This property affects the magnitude of the pressure that the bladder is able to generate. For instance, in the preferred application of these bladders in devices for infusing liquid medicaments when the stress at 300% elongation is below 50 psi the resulting pressure is too low to permit precise infusion into a living body.

The two characteristics of the bladders of this invention that primarily distinguish them from the prior art bladders are the low degree of stress relation of the elastomer and the low degree of low frequency hysteresis of the elastomer. These characteristics are extremely important to achieving constancy of deflation pressure and are the principal factors why the deflation curves (Curve C in FIG. 1) of the bladders essentially retrace their inflation curves (Curve B in FIG. 1). Specifically, the elastomer has a stress relaxation of less than about 10% and a low frequency hysteresis of less than about 10%. Some elastomeric compositions have excellent high frequency hysteresis; that is, they exhibit low hysteresis levels upon rapid elongation and contraction. They have, however, poor low frequency hysteresis; that is, they exhibit high degrees of hysteresis upon elongation and contraction over long periods of time. Conventional sulfur-cured natural rubber is an example of a material which has a good high frequency hysteresis but has an unacceptable degree of low frequency hysteresis. Stress relaxation is measured by preparing samples of the elastomeric composition according to ASTM 412-68 (Die C), elongating the samples to 300% at 2.0 in/min on an Instron tensile tester, maintaining the samples at that elongation for approximately 1 day, and retracting the samples at the same speed as used for elongating them. Stress relaxation is calculated by dividing the difference between (1) the stress immediately after elongation and (2) the stress immediately before retraction by (1). Low frequency hysteresis is measured in the same manner as stress relaxation except that the samples are retracted immediately after elongation. Hysteresis is expressed as the percent difference between the integral of the stress/strain curve for elongation and the integral of the stress/strain curve for retraction.

In embodiments of the dispenser in which the bladder is enclosed within a housing or other framework, it is critical that the bladder be enclosed such that it is substantially free from any restraints which constrict it in its inflated and deflated states in order to maintain substantial constancy in the deflation pressure. Such restraints cause pressure variation both by adding friction factors to the deflation as well as by interfering with, or even overriding, the ideal elastomeric properties of the bladders.

Examples of elastomers that have the characteristics required for use in this invention are vulcanized synthetic polyisoprenes that have a significant proportion, but not all, of their monomeric units joined with a cis orientation. More specifically, it is preferred if from about 85% to about 98% of the monomeric units have cis bonding. If more than 98% of the bonds are of a cis orientation, the resulting polymer will be too crystalline and not have the desired elastomeric properties. If less than 85% of the bonds are cis, the elastomeric properties may suffer as well. The most preferred polyisoprenes have about 90% to about 98% cis orientation. Minor amounts of appropriate rubbers, such as butadiene rubber and natural rubber, may be blended with the polyisoprene if desired. Additives such as fillers, reinforcing agents, anti-oxidants, pigments, and the like may also be formulated with the polyisoprene. However, care must be used in such formulation in order to avoid deleteriously affecting the performance of the bladder.

The above described polyisoprenes are vulcanized to form carbon-to-carbon or monothio cross-links in the polymer network. After vulcanization, the polyisoprene is characterized by extremely low decay of stress when stretched to constant extension, very low hysteresis on extension and contraction, and very low permanent set. The cross-link density of the vulcanized polymer will usually be about 16 to about 24 cross-links per polyisoprene molecule (M/Mc in the Flory-Rehner equation). Organic peroxides may be used as vulcanizing agents to form the carbon-to-carbon cross-linked variety of polyisoprene and thiuram disulfides may be used to form the monothio cross-linked variety. Organic peroxides are preferred vulcanizing agents and the carbon-to-carbon cross-linked polyisoprene is correspondingly preferred. The quantity of vulcanizing agent significantly affects the relevant mechanical properties of the vulcanisate. Too much agent will result in brittleness; whereas too little will result in poor hysteresis, stress decay, and permanent set. In the case at hand, concentrations of about $5.5 \times 10^{-3}$ to about $7.5 \times 10^{-3}$ moles of active peroxide per 100 g of polyisoprene have been found to be useful, with about $6.7 \times 10^{-3}$ moles of active peroxide per 100 g of polyisoprene being preferred.

Peroxides that may be used as vulcanizing agents in the invention include benzoyl peroxide, 1,1-di-t-butylperoxy-3,3,5-trimethylcyclohexane, n-butyl-4,4-bis(t-butylperoxy)valerate, $\alpha, \alpha'$-bis(t-butylperoxy)diisopropylbenzene, di-t-butyl peroxide, and dicumyl peroxide. Dicumyl peroxide is preferred. Sulfides that may be used as vulcanizing agents include tetramethyl thiuram disulfide, tetraethyl thiuram disulfide and 4,4'-dithiomorpholine. Tetramethyl thiuram disulfide is preferred.

The bladders of this invention may be fabricated by casting, extruding, dipping of a mandrel and like processes known to the art. The only limitations on fabrication method derive from failures of the products to meet the above-noted critical criteria.

The bladders of the present invention are used to store and deliver fluids, including pure liquids, solutions, gels, suspensions and the like at a constant pressure optionally over a prolonged period of time, for example, up to about 30 days or longer. Such bladders thus find application in a wide range of uses for dispensing medical fluids, biological agents, insecticides, anti-fouling compounds, odorants, water treatment chemicals, detergents, antiseptics, insect repellants, reaction catalysts and nutritional fluids to name but a few.

A preferred application of the bladders of this invention is in devices for the administration of drugs over periods of from about one to about 24 hours or, more specifically, devices for the infusion of drugs into the bodies of humans or other living creatures. In such devices, in combination with means for restricting the flow of liquids to a very low rate, these bladders make possible compact devices for infusing drugs under pressure at constant rates. Devices employing this invention have numerous advantages. For example, they overcome the use of cumbersome gravity-fed intravenous "drip" systems. Also, by their small size and positional insensitivity (since they operate independent of gravity) they may be fastened to the user and permit the user to be ambulatory. Further, the devices offer the advantage of being able to administer very small flows of drug, such as 0.1 to 1 ml of drug/hour. The prior art "drip" systems are most difficult to calibrate or control at rates much lower than about 10 ml/hour. This decrease in volume of delivered fluid is of benefit in many conditions, such as in heart disease, whereit is undesirable to increase circulatory system volume even by a small amount.

Device 10, as shown in FIG. 6, could easily function as a drug infusion device. First, the drug to be infused would be pumped into bladder 11 and valve 16 would be closed. A suitable tube and needle or catheter (not shown) would be affixed to tube 17, valve 16 would be opened, and drug would be permitted to flow through the tube and needle at a rate controlled by flow control valve 16. The needle could be inserted into an artery or vein and the drug infused thereinto. The delivery device might, if desired, be affixed to the patient by, for example, straps, tape or the like, thus permitting the patient to be ambulatory.

Figure 8:
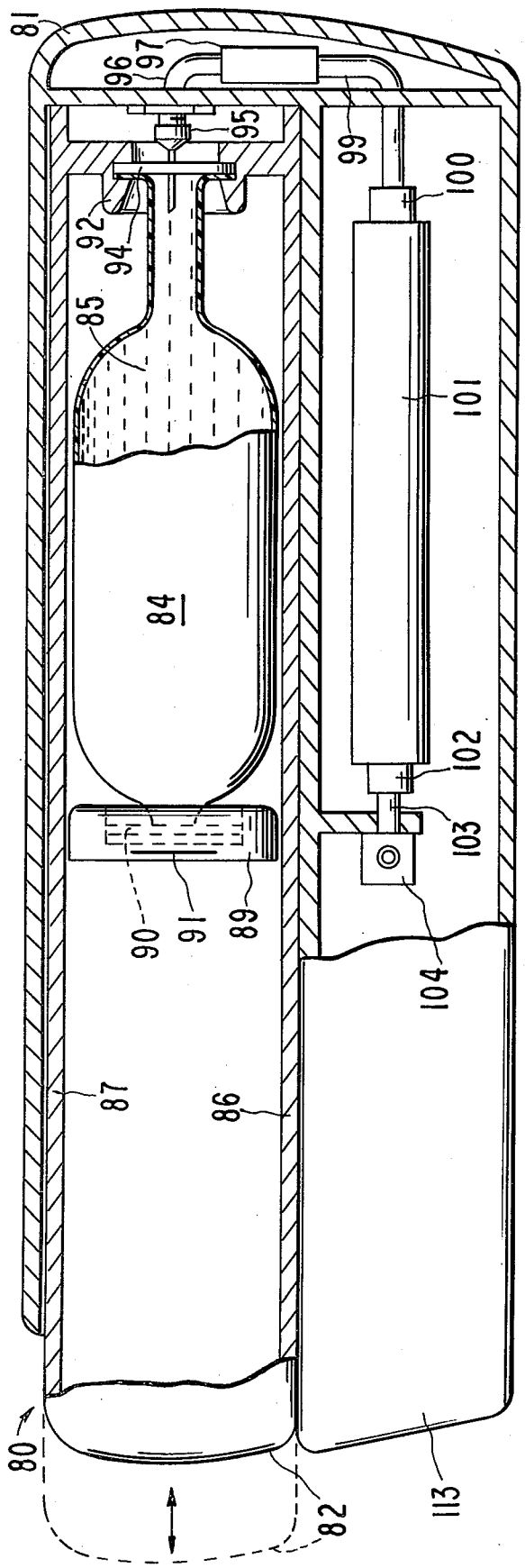
FIG. 8 is a partly cross-sectional top view of a device embodying the invention adapted for infusing drugs into a patient.

A more sophisticated drug infusion device embodying the novel and useful bladders of this invention is depicted as device 80 in FIG. 8. Device 80 comprises a structural base 81 in which the elements of the drug infusion device are mounted. In practice, base 81 is made up of one or several plastic castings and presents a closed smooth surface. Here it is shown cut away. Auxiliary base 82 slidably engages base 81 and is held in the relation shown by latches or similar fastening means. Located within auxiliary base 82 is elastomeric bladder 84, dimensioned and of a material in accord with this invention. Bladder 84 is filled with and distended or inflated by liquid medicament 85. Walls 86 and 87 of auxiliary base 82 enclose bladder 84 but are positioned so as not to significantly touch or restrict bladder 84 in either inflated or deflated form. One end of bladder 84 is affixed to slide 89 via fastening seal 90. Slide 89 functions to smooth the contraction of bladder 84 and to indicate by mark 91 and a scale (not shown) on auxiliary base 82 the extent of expansion of bladder 84 and hence how much drug it contains. Slide 89 and seal 90 may be adapted with the addition of septums, valves or the like to permit the charging of drug into bladder 84 or the bleeding of gas (air) from the bladder. The end of bladder 84 distal from slide 89 fixably engages auxiliary base 82 via clamp ring 92. This end of bladder 84 is equipped with connecting means through which connection can be made between liquid medicament 85 and the remainder of the device. In FIG. 8 this connecting means comprises a penetrable septum sealing the end of bladder 84, which septum may be penetrated by hollow needle 95. Alternative arrangements, such as a position-controlled valve or the like could also be employed. When bladder 84 is connected via septum 94 and needle 95, liquid medicament is forced via the elastic pressure of bladder 84 through needle 95 to conduit 96, filter 97, conduit 99 and connector 100 to flow control 101. Filter 97 is an optional component. It is often useful to prevent particulate matter from interfering with the flow control. Flow control 101 consists of a variable restriction or valve which throttles and regulates the flow of liquid from bladder 84. While higher and lower flow rates and pressures may be employed, bladder 84 and flow control 101 are generally designed to permit the delivery of from 0.1 to 5.0 ml per hour of drug at pressures of from 2 to 75 psi.

The volume of drug 85 in bladder 84 may range from about 10 ml to about 75 ml. Generally for a portable drug delivery unit, the volume of drug 85 is from 10 ml to 40 ml.

Figure 9:
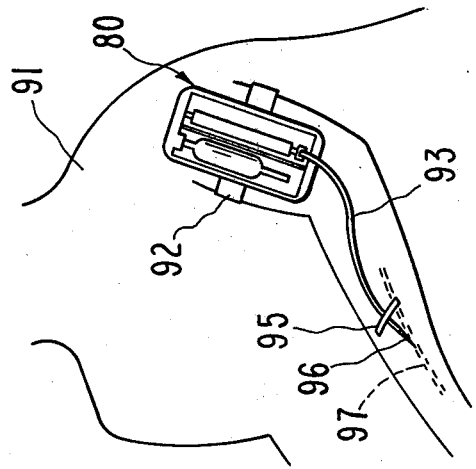
FIG. 9 is a perspective elevational view of the device depicted in FIG. 8, in use administering drugs.

The flow of drug from flow control 101 passes via connector 102 and conduit 103 to fitting 104 and from there is infused into a patient as shown in FIG. 9. In FIG. 9, a human torso 83 is illustrated having delivery device 80, as set forth in FIG. 8, attached to its left arm by strap or tape 88. Tube 93 leads from fitting 104 (not shown) in device 80 and conducts drug therefrom to vein or artery 94 via needle 98. Tape 105 holds tube 93 and needle 98 in place.

The following examples set forth illustrative embodiments of the invention. These embodiments are not to be construed as limiting the scope of the invention.

EXAMPLE 1

A 1000 gram portion of solid Ameripol SN 600 brand polyisoprene, having a 92–98% cis content, is placed in a mill and masticated at 120° F, 18 grams of dicumyl peroxide are thoroughly blended through the polyisoprene and the mixture is extruded as a 1/10 in. thick sheet. This polyisoprene has a stress at 300% elongation of 260 psi, an ultimate elongation of 550%, a permanent set at break less than 1%, a stress relaxation of 3%, and a low frequency hysteresis of less than 2%. Two pieces of this sheet are laid in a compression mold which has four cavities, each shaped to give a hollow cylindrical bladder having an inside diameter of 150 in., an outside diameter of 3/16 in., a wall thickness of 1/32 in. and a length of 3 in. The mold is compressed about the two pieces of rubber sheet and held under pressure at 330° F for 20 minutes. During this period the polyisoprene is formed to the shape of the mold and the polyisoprene is cross-linked by the peroxide. The mold is opened and the polyisoprene tubes are removed.

Another of the bladders is attached to a water supply and a metering valve filled with 30 ml of water and the valve then closed. There is a pressure gauge attached to the bladder, upstream of the metering valve. The inflated bladder is a cylindrical "sausage". The pressure inside the bladder is 600 mm of mercury. The valve is opened to permit a flow of about 1 to 1.1 ml/hr of water from the bladder. The pressure is monitored as the bladder deflates and is found to vary between 600 and 565 mm during deflation from 30 ml to 2 ml (less than a ± 10% variation from the mean). Below 2 ml it drops rapidly. The total volume of liquid expelled is 29 ml, or 97% of the original.

EXAMPLE 2

A 1000 gram portion of solid Ameripol SN 600 brand polyisoprene, having a 92–98% cis content, is placed on a rubber mill and masticated at 150° F, 18 grams of dicumyl peroxide ($6.67 \times 10^{-3}$ moles of peroxide per 100 grams polyisoprene) are thoroughly blended through the polyisoprene and the mixture is sheeted as a 0.1 in. thick sheet. The physical properties of this polyisoprene are the same as the polyisoprene of Example 1. A 10 gram portion of the mixture was inserted into a six cavity transfer mold to form cylindrical bladders having an inside diameter of 0.124 in., an outside diameter of 0.174 in., and a length of about 1.6 in. Such a bladder meets the geometrical limitations preferred with the present invention, having a wall thickness equal to 0.20 time the inside diameter and a length which is 9 times the outside diameter. The rubber is cured under pressure at 330° F for 20 minutes.

One of the resulting bladders is attached to a water supply and a metering valve filled with 25 ml of water and the valve then closed. There is a pressure gauge attached to the bladder, upstream of the metering valve. The inflated bladder is a cylindrical "sausage". The pressure inside the bladder is 10.7 psi. The valve is opened to permit a flow of about 10 ml/hr of water from the bladder. The pressure is monitored as the bladder deflates and is found to vary between 11.6 and 10.1 psi during deflation from 25 ml to 2 ml (less than a ± 10% variation from the mean). The total volume of liquid expelled is 24.5 ml, or 98% of the original.

EXAMPLE 3

The experiment of Example 2 is repeated substituting 46 grams of Percadox 17/40 brand of n-butyl-4,4-bis(t-butylperoxy)valerate for the dicumyl peroxide. This polyisoprene has a stress at 300% elongation of 250 psi, an ultimate elongation of 560%, a permanent set at break of less than 1%, a stress relaxation of 8%, and a low frequency hysteresis of 4%. The resulting reservoir had a static pressure of 10.3 psi. During deflation from 25 ml to 3 ml the pressure varied from 11.3 to 9.4 psi. The total volume expelled was 24.5 ml or 98% of the original volume.

EXAMPLES 4 & 5

The experiment of Example 2 is repeated with polyisoprene having varying levels of dicumyl peroxide. The results of these experiments are reported below:

| Moles of Peroxide per 100 g of Polyisoprene | Static Pressure, psi |
|---|---|
| $5.9 \times 10^{-3}$ | 9.1 |
| $7.4 \times 10^{-3}$ | 12.0 |

These polyisoprenes have stresses at 300% elongation of 900 and 875 psi, respectively, ultimate elongations of 650% and 420%, respectively, permanent sets at break of less than 1%, low frequency hysteresis of 3% and 5%, respectively, and stress relaxations of 4% and 8%, respectively. In both cases better than 95% of the bladder contents were delivered.

EXAMPLE 6

The experiment of Example 1 is repeated using a polyisoprene composition of the following formula, cured for 20 min. at 310° F:

| phr | Ingredient | Grams |
|---|---|---|
| 100 | Ameripol SN 600 polyisoprene | 50 |
| 3 | Stearic Acid | 1.5 |
| 4 | Zinc Oxide | 2 |
| 4 | Tetramethyl thiuram disulfide (TMTD) | 2 |

This polyisoprene has a stress at 300% elongation of 200 psi, an ultimate elongation of 700%, a permanent set at break of less than 1%, a stress relaxation of 6%, and a low frequency hysteresis of 3%. The resulting bladder is inflated with 25 ml liquid giving a static pressure of 10.35 psi. The pressure varies from 10.7 to 9.3 psi during the deflation from 25 ml to 3 ml.

Modifications of the above described invention that are obvious to those of skill in the relevant arts are intended to be within the scope of the following claims.

We claim:

1. In a liquid dispensing apparatus comprising in combination a housing, an expansible elastomeric bladder contained within the housing for holding the liquid under pressure, the elastic force in the bladder walls providing the force by which the liquid is dispensed from the apparatus, a liquid flow passageway extending from the bladder to a dispensing site and valve means associated with the passageway for regulating the flow of liquid through the passageway, said bladder being cylindrical, having a deflated length that is not less than 5 times its deflated inside diameter, walls whose thickness is from about 0.01 to about 1 times the deflated inside diameter of the bladder, and an axial stress at 300% elongation that is not more than 1.5 times the radial stress at 300% elongation, and being formed from an elastomeric composition that has a permanent set of less than about 3% and that has a uniaxial stress/strain curve that has an ultimate elongation exceeding 400%, and a point in the range of 300% and 1000% elongation at which the slope increases significantly, the improvement wherein the elastomeric composition has a stress relaxation that does not exceed about 10% and a low frequency hysteresis that does not exceed about 10%.

2. The liquid storing and dispensing apparatus of claim 1 including the further improvement wherein the bladder is contained within the housing in a manner in which the bladder is substantially unrestricted in its deflated and inflated states.

3. The liquid storing and dispensing apparatus of claim 1 wherein the thickness of the bladder walls is from 0.1 to 0.5 times the deflated inside diameter of the bladder.

4. In an apparatus for infusing liquid drug under pressure into a patient comprising in combination a housing, an expansible elastomeric bladder contained within the housing for holding the liquid drug under pressure, the elastic force in the bladder walls providing the force by which the liquid drug is infused, a liquid drug passageway extending from the bladder to the infusion site and valve means associated with the passageway for regulating the flow of liquid drug through the passageway, said bladder being cylindrical, having a deflated length that is not less than 5 times its deflated inside diameter, walls whose thickness is from about 0.01 to about 1 times the deflated inside diameter of the bladder, and an axial stress at 300% elongation that is not more than 1.5 times the radial stress at 300% elongation, and being formed from an elastomeric composition that has a permanent set of less than about 3% and that has a uniaxial stress/strain curve that has a stress exceeding 50 psi at 300% elongation, an ultimate elongation exceeding 400%, and a point in the range of 300% and 1000% elongation at which the slope increases significantly, the improvement wherein the elastomeric composition has a stress relaxation that does not exceed about 10% and a low frequency hysteresis that does not exceed about 10%.

5. The apparatus of claim 4 including the further improvement wherein the bladder is contained within the housing in a manner in which the bladder is substantially unrestricted in its deflated and inflated states.

6. The apparatus of claim 4 wherein the thickness of the bladder walls is from 0.1 to 0.5 times the deflated inside diameter of the bladder.

* * * * *

UNITED STATES PATENT AND TRADEMARK OFFICE
Certificate

Patent No. 3,993,069 Patented November 23, 1976

Richard G. Buckles, Harold M. Leeper, Su Il Yum and Alan S. Michaels

Application having been made by Richard G. Buckles, Harold M. Leeper, Su Il Yum and Alan S. Michaels, the inventors named in the patent above identified, and Ciba-Geigy Limited, the assignee, for the issuance of a certificate under the provisions of Title 35, Section 256, of the United States Code, deleting the names of Su Il Yum and Alan S. Michaels as joint inventors, and a showing and proof of facts satisfying the requirements of the said section having been submitted, it is this 6th day of May 1980, certified that the names of the said Su Il Yum and Alan S. Michaels are hereby deleted from the said patent as joint inventors with the said Richard G. Buckles and Harold M. Leeper.

FRED W. SHERLING,
*Associate Solicitor.*